United States Patent [19]

Tomoi

[11] Patent Number: 5,202,331
[45] Date of Patent: Apr. 13, 1993

[54] THERAPEUTIC AGENT FOR DYSURIA COMPRISING A-PHENYL-A-PYRIDYLALKANOIC ACID DERIVATIVES

[75] Inventor: Masaaki Tomoi, Osaka, Japan

[73] Assignee: Fujisawa Pharmaceutical Co., Ltd., Osaka, Japan

[21] Appl. No.: 678,244

[22] Filed: Apr. 1, 1991

[30] Foreign Application Priority Data

Apr. 18, 1990 [JP] Japan .................. 2-103903

[51] Int. Cl.$^5$ .................. A61K 31/435; A01N 43/40
[52] U.S. Cl. .................. 514/277; 546/333
[58] Field of Search .................. 514/277

[56] References Cited

U.S. PATENT DOCUMENTS

| 4,564,621 | 1/1986 | Ueda et al. | 514/357 |
| 4,766,213 | 8/1988 | Juraszyk et al. | 544/127 |
| 4,857,535 | 8/1989 | Davis | 514/317 |
| 4,957,941 | 9/1990 | Davis | 514/648 |

FOREIGN PATENT DOCUMENTS

| 0105458 | 4/1984 | European Pat. Off. |
| 105458 | 11/1989 | European Pat. Off. |
| 0383256 | 8/1990 | European Pat. Off. |

OTHER PUBLICATIONS

The American Journal of Surgery, vol. 145, No. 5, May 1983, pp. 558–561; J. D. Giesy et al.: "Micturition Neuropharmacology".

Clinics in Ohstetrics and Gynaecology, vol. 8, No. 1, Apr. 1981, pp. 149–160, W. B. Saunders Co., Ltd.; F. B. Gibberd: "The Neurogenic Bladder".

Arch. Intern. Med., vol. 143, Sep. 1983, pp. 1683–1686; L. H. Danziger et al.: "Disopyramide-Induced Urinary Retention".

The Merck Manual, 15th edition, 1987, p. 1553, edited by R. Berkow et al, Merck & Co., Inc., Rahway, N.J. US.

Medicinal Chemistry 3rd ed., Wiley–Interscience New York, N.Y. p. 76 (1970).

Oyo Yakuri/Pharmacometrics 39(6):595–599, 1990.

Merck Index 10th ed., Merck & Co., Rahway, N.J. 1983, p. 68.

Primary Examiner—Frederick E. Waddell
Assistant Examiner—Fred Tsung
Attorney, Agent, or Firm—Oblon, Spivak, McClelland, Maier & Neustadt

[57] ABSTRACT

A method for the therapeutic treatment of dysuria with alpha-phenyl-alpha-pyridylakanoic acid derivatives is disclosed.

2 Claims, No Drawings

THERAPEUTIC AGENT FOR DYSURIA COMPRISING A-PHENYL-A-PYRIDYLALKANOIC ACID DERIVATIVES

This invention relates to a therapeutic agent for dysuria comprising α-phenyl-α-pyridylalkanoic acid derivatives or their salts.

Accordingly, the object of this invention is to provide a therapeutic agent for dysuria comprising α-phenyl-α-pyridylalkanoic acid derivatives of the following formula [I] or their salts:

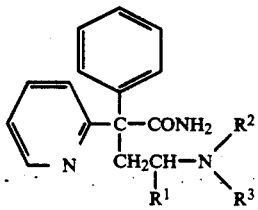

wherein $R^1$, $R^2$ and $R^3$ are each lower alkyl.

It is known as described in European Patent Application publication No. 105458 that the compound [I] of this invention has antiulcer activity and antispasmodic activity. Therefore, the compound is expected to be useful for the management of spasm, pain and/or hyperanakinesia in gastric ulcer, duodenal ulcer, hyperacidity, esophagospasm, gastritis, enteritis, irritable bowel syndrome, intestinal colic, cholecystitis, cholangitis, pylorospasm, pancreatitis, biliary dyskinesia, sequelae of cholecystectomy, urolithiasis, dysmenorrhea, hyperhidrosis, urinary tract spasm or the like.

However, it is not known that this compound is effective in the treatment of dysuria such as pollakiuria, urinary urgency, incontinence of urine or the like.

Particulars of the various definitions mentioned in this specification and preferred examples thereof are explained in the following.

The term "lower" used in this specification is intended to mean a group having 1 to 6 carbon atoms and preferably 1 to 4 carbon atoms, unless otherwise provided.

Suitable "lower alkyl" may be straight or branched one such as methyl, ethyl, propyl, isopropyl, butyl, tert-butyl, pentyl, hexyl or the like, in which the most preferable one is methyl.

Suitable salts of the compound [I] are conventional non-toxic pharmaceutically acceptable salts and may include an organic or inorganic acid addition salt [e.g. formate, acetate, fumarate, citrate, trifluoroacetate, maleate, tartrate, methanesulfonate, benzenesulfonate, toluenesulfonate, hydrochloride, hydrobromide, sulfate, phosphate, etc.], or the like.

It is to be noted that each of the compound [I] may include one or more stereoisomers due to asymmetric carbon atom(s), and all of such isomers and a mixture thereof are included within the scope of this invention.

In order to show the usefulness of the compound [I] or their salts used as an ingredient of the therapeutic agent for dysuria, the results of pharmacological tests are shown in the following.

TEST COMPOUND (±)-(2R*,4R*)-4-Dimethylamino-2-phenyl-2-(2-pyridyl)-valeramide

TEST 1

Inhibition of urinary bladder contraction in the pressure-loaded hyperactive bladder model in rats

[I] Method

Male S.D. rats weighing 240–450 g were anesthetized with urethane (1.0 g/kg) s.c.. The urinary bladder was then exposed through a midline incision in the abdomen and the intravesical pressure was recorded. Thus, a balloon attached to one end of a stainless steel tube (1.2 mm in outer diameter, 5 cm in length) was inserted into the bladder through a small incision made in the bladder dome, while the other end of the tube was connected to a pressure transducer. The ureter was ligated and cut and a polyethylene cannula was inserted from the proximal cut end to drain off the urine.

Hyperactive bladder (detrusor hyperreflexia) was induced by water filling of the bladder. A hydrostatic pressure of about 10 mmHg was applied to the balloon in the bladder.

When the contractile response of the bladder to water pressure loading became steady, the test compound was administered intravenously.

[II] Result $ED_{30} = 0.09$ mg/kg

Test 2

Effect on voidinc reflex bladder contraction in rats with the ureter ligated

[I] Method

A midline incision was made in the abdomen of male S.D rats (body weight 250–350 g) under urethane (1.0 g/kg i.p.) anesthesia. A small incision was made in the bladder dome and one end of a polyethylene tube was inserted and, then, ligated. To the other end of the polyethylene tube was attached a three-way cock. An infusion pump was connected to one of the joints and a transducer was connected to another joint for measurement of the intravesical pressure. Physiological saline was then infused continuously into the bladder. After confirmation of steady voiding reflexes, the ureter was ligated immediately before the next voiding and the infusion of physiological saline was stopped. After the resulting rhythmic contractions became stable, the test compound was administered into the jugular vein to evaluate its effect.

[II] Result $ED_{50} = 0.56$ mg/kg

TEST 3

Anticholinergic effect in the isolated guinea pig bladder

[I] Method

Male guinea pigs weighing 400–700 g were fainted and killed by a blow on the occipital region. A bladder detrusor muscle specimen (15–20 mm long × 5 mm thick) was prepared by longitudinal section and suspended in a Magnus bath containing Krebs solution which was aerated with 95% $O_2$–5% $CO_2$. Isotonic contractions were recorded through a tension transducer. The buffer solution was changed five times at 15-minute intervals. The equilibration time was 10 minutes. Contractions were induced with 10 μM carbamylcholine, and after the contractions became steady, the test compound was added to the Magnus bath and its anticholinergic effect was investigated.

[II] Result $IC_{50} = 6.0 \times 10^{-7}$ g/ml

TEST 4

Acute toxicity test

[I] Method

Five rats (Crj:CD(SD)) strain) of either sex were used per group. Solutions of the test compound were prepared as shown below and administered to rats intravenously or subcutaneously. The rats were then observed for 14 days. The $LD_{50}$ values were calculated by the probit method. (Preparation of test solutions)

The test compound was dissolved in hydrochloric acid and the solution was adjusted to pH 6–7 with sodium hydrogen carbonate and diluted with physiological saline to the required concentrations.

[II] Results

| Animal | Route of administration | Sex | $LD_{50}$ (mg/kg) |
|---|---|---|---|
| Rats (Crj:CD (SD)) | i.v. | Male | 47.2 |
| | | Female | 42.3 |
| | s.c. | Male | 922 |
| | | Female | 915 |

It is clear from the above results that the compound [I] has anticholinergic activity and exhibits an inhibitory effect on bladder contraction. This means that the compound is a useful therapeutic agent for dysuria such as pollakiuria, urinary urgency, incontinence of urine or the like in cases of nervous pollakiuria, neurogenic bladder, nocturia, unstable bladder, cystospasm, chronic cystitis, chronic prostatitis, or the like.

Since the compound of the invention, thus, has anticholinergic activity, it is expected to be also useful for the treatment of asthma, angina pectoris, or the like.

The therapeutic agent for dysuria used in the present invention can be administered orally, parenterally or externally (topically) to a mammal including human being in a conventional pharmaceutical form such as capsules, micro-capsules, tablets, granules, powders, troches, pills, ointments, suppositories, injection solutions, suspensions, syrups, and the like.

The therapeutic agent for dysuria of the present invention can be produced by the established procedures using various organic or inorganic carriers, which are conventional for pharmaceutical purpose, such as excipient [e.g. sucrose, starch, mannit, sorbit, lactose, glucose, cellulose, talc, calcium phosphate, calcium carbonate, etc.], binding agent [e.g. cellulose, methyl cellulose, hydroxymethyl cellulose, polypropylpyrolidone, gelatin, gum arabic, polyethylene glycol, sucrose, starch, etc.], disintegrator [e.g. starch, carboxymethyl cellulose, hydroxypropyl starch, sodium bicarbonate, calcium phosphate, calcium citrate, etc.], lubricant [e.g. magnesium stearate, aerosil, talc, sodium laurylsulfate, etc.], flavoring agent [e.g. citric acid, menthol, glycine, orange powders, etc.], preservative [e.g. sodium benzoate, sodium bisulfite, methylparaben, propylparaben, etc.], stabilizer [e.g. citric acid, sodium citrate, acetic acid, etc.], suspending agent [e.g. methyl cellulose, polyvinylpyrrolidone, aluminum stearate, etc.], dispersing agent [e.g. hydroxypropylmethyl cellulose, etc.], diluting agent [e.g. water, etc.], base wax [e.g. cacao butter, white petrolatum, polyethylene glycol, etc.].

The amount of the active ingredient in such a pharmaceutical preparation may be no more than the amount necessary to produce the desired therapeutic effect. By way of illustration, it can be about 0.2 mg to about 500 mg per unit dose for oral or parenteral administration.

The active ingredient can be administered in a unit dose of 0.1 mg/patient to 500 mg/patient once to 4 times a day. It should be understood that the above dosage may be adjusted according to the patient's age and body weight, the severity of condition and the route and method of administration.

The following Preparation and Examples are given for the purpose of illustrating this invention in more detail.

PREPARATION (1) A mixture of 4-dimethylamino-2-phenyl-2-(2-pyridyl)-valeronitrile (50.0 g), water (2.74 g) and sulfuric acid (50 ml) was reacted at 100–105° C. for 2 hours. The reaction mixture was then cooled, diluted with cold water (100 ml) and poured into a mixture of methylene chloride (400 ml) and water(500 ml). The aqueous layer was adjusted to pH 12.5 with 24% aqueous sodium hydroxide solution. The organic layer was taken, washed with saturated aqueous sodium chloride solution and dried over anhydrous magnesium sulfate. To this were added isopropyl alcohol (75 ml), acetone (175 ml) and concentrated hydrochloric acid (10.87 g) and the mixture was stirred for 10 minutes. Then, seed crystals (0.05 g) were added and the mixture was further stirred at 25–30° C. for 1 hour and, then, at −5° to −10° C. for another 1 hour. The resulting crystals were recovered by filtration, washed with methylene chloride and dried to give (±)-(2R*,4R*)-4-dimethylamino-2-phenyl-2-(2-pyridyl)valeramide hydrochloride (26.9 g).

(2) To a solution of (±)-(2R*,4R*)-4-dimethylamino-2-phenyl-2-(2-pyridyl)valeramide hydrochloride (20 g) in water (80 ml) were added seed crystals (0.02 g) and a solution of sodium hydroxide (2.47 g) in water (80 ml) was dropwise added thereto at 20–25° C. over a period of 30 minutes. The mixture was stirred at the same temperature for 1 hour. The resulting crystals were recovered by filtration, washed with water and dried to give (±)-(2R*,4R*)-4-dimethylamino-2-phenyl-2-(2-pyridyl)-valeramide (16.1 g).

mp : 156°–157° C.

EXAMPLE 1

(±)-(2R*,4R*)-4-Dimethylamino-2-phenyl-2-(2-pyridyl)-valeramide (120 g), lactose (1080 g) and low-substituted hydroxypropylcellulose (110 g) were blended together. To this blend was added a solution of hydroxypropylcellulose L (23 g) in water (2.4 kg) dropwise. After compounding, the mixture was dried and sieved through a 20-mesh screen for size selection. To the resulting granulation was added magnesium stearate (11 g), followed by mixing. The granules thus obtained were compressed into tablets (135 mg/tablet).

EXAMPLE 2

Instead of being compression-molded, the granules obtained in Example 1 were encapsulated to provide capsules (80 mg/capsule).

What we claim is:

1. A method for the therapeutic treatment of dysuria which comprises administering an effective amount of a compound of the formula:

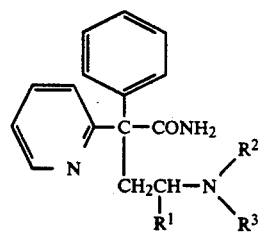

wherein $R^1$, $R^2$ and $R^3$ are each lower alkyl, or its salt to human beings or animals in need of treatment.

2. A method according to claim 1 which comprises administering (±)-(2R*,4R*)-4-dimethylamino-2-phenyl-2-(2-pyridyl)valeramide.

* * * * *